United States Patent
Guidotti et al.

[11] Patent Number: 6,123,692
[45] Date of Patent: Sep. 26, 2000

[54] ABSORBENT ARTICLE HAVING A FRONT URINE-COLLECTING PART AND A REAR FAECES-COLLECTING PART

[75] Inventors: Ted Guidotti, Göteborg; Anders Gustafsson, Billdal; Urban Widlund, Mölnlycke, all of Sweden

[73] Assignee: SCA Hygiene Products AB, Goteborg, Sweden

[21] Appl. No.: 08/849,320

[22] PCT Filed: Dec. 15, 1995

[86] PCT No.: PCT/SE95/01520

§ 371 Date: Jun. 30, 1997

§ 102(e) Date: Jun. 30, 1997

[87] PCT Pub. No.: WO96/20666

PCT Pub. Date: Jul. 11, 1996

[30] Foreign Application Priority Data

Dec. 30, 1994 [SE] Sweden ................... 9404567

[51] Int. Cl.[7] .............. A61F 13/15; A61F 13/20
[52] U.S. Cl. ................ 604/385.01; 604/385.19; 604/378
[58] Field of Search ............... 604/385.1, 348, 604/378, 379, 380, 385.01, 385.19

[56] References Cited

U.S. PATENT DOCUMENTS

| | | | |
|---|---|---|---|
| 3,532,093 | 10/1970 | Lovret | 604/348 |
| 3,848,599 | 11/1974 | Scheer | 604/385.1 |
| 4,950,263 | 8/1990 | Lewd | 604/385.1 |
| 4,988,344 | 1/1991 | Reising et al. | 604/380 |
| 5,062,840 | 11/1991 | Holt et al. | 604/385.1 |
| 5,134,007 | 7/1992 | Reising et al. | 604/385.1 |
| 5,554,142 | 9/1996 | Dreier et al. | 604/385.1 |
| 5,746,730 | 5/1998 | Suzuki et al. | 604/385.1 |

FOREIGN PATENT DOCUMENTS

| | | | |
|---|---|---|---|
| 0 355 740A2 | 2/1990 | European Pat. Off. | |
| 2495899 | 6/1982 | France | 604/385.1 |
| 2022026 | 11/1991 | Spain | 604/385.1 |
| 2268073 | 1/1994 | United Kingdom | 604/385.1 |
| WO 94/14395 | 7/1994 | WIPO | |
| WO 95/25493 | 9/1995 | WIPO | |

*Primary Examiner*—Mark O. Polutta
*Attorney, Agent, or Firm*—Burns, Doane, Swecker & Mathis, L.L.P.

[57] ABSTRACT

An absorbent article such as a diaper, an incontinence guard or the like in which the top sheet (1) of the article includes a transverse barrier (11) which divides the article into a rear and a front part (4, 6) and which is intended to prevent faeces discharged to the rear part of the top sheet from moving to the front part thereof. Arranged in the absorbent body (3) essentially opposite the top sheet barrier (11) is a liquid barrier (21) which prevents, either completely or partially, the transportation of liquid in the absorbent body from the front part of the article to the rear part thereof, at least in the layer (18) of the absorbent body that lies proximal to the wearer in use.

23 Claims, 2 Drawing Sheets

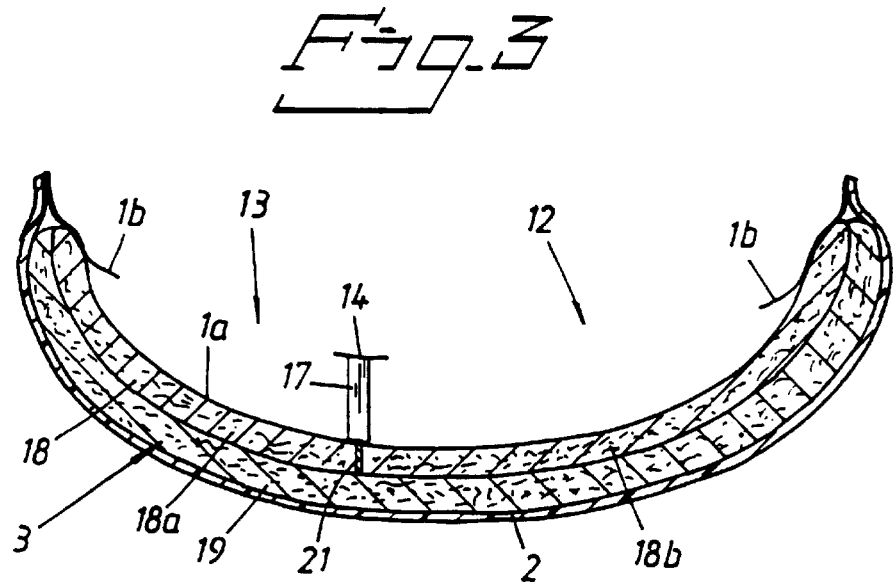
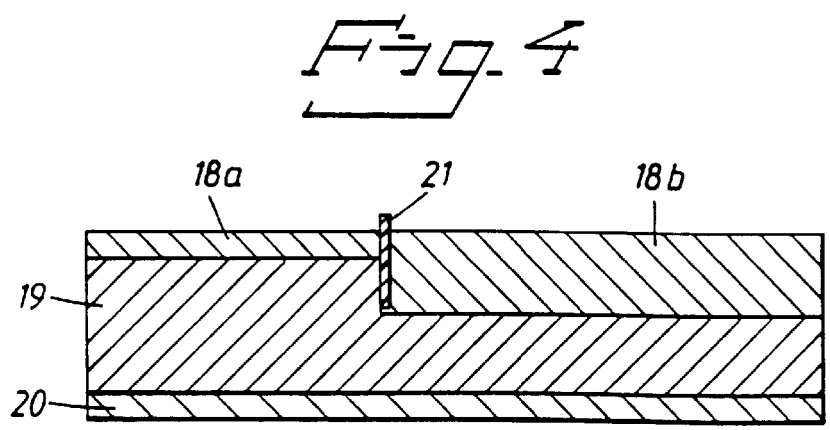
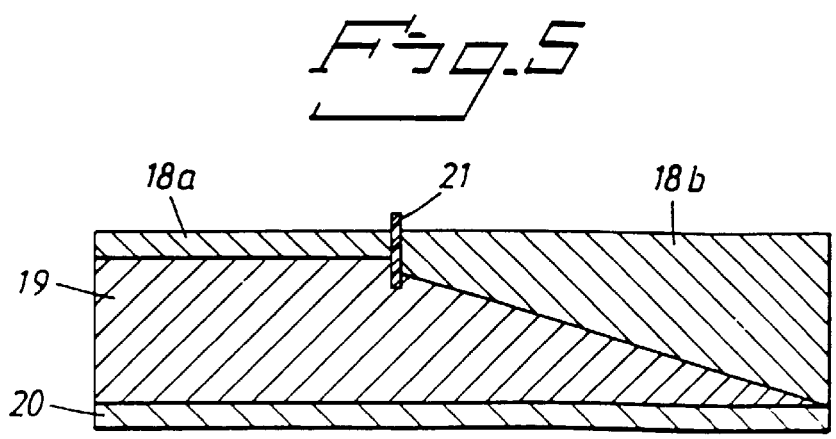

ABSORBENT ARTICLE HAVING A FRONT URINE-COLLECTING PART AND A REAR FAECES-COLLECTING PART

TECHNICAL FIELD

The present invention relates to an absorbent article, such as a diaper, pants-type diaper, an incontinence guard or like article which includes a liquid-permeable top sheet, a liquid-impermeable bottom sheet and an absorbent body disposed therebetween, wherein the top sheet includes a transverse barrier which divides the article into a front and a rear part and which is intended to prevent faeces discharged to the rear part of the article moving to the front part thereof.

BACKGROUND OF THE INVENTION

It is known to provide the top sheets of diapers with transverse barriers for the purpose of preventing faeces from spreading to the front part of the diaper. EP-A-0,355,740 teaches such transverse barriers, which are created either by fastening strings of plastic foam to the top sheet or by creating transverse folds or pleats with the aid of elastic devices which extend in the longitudinal direction of the diaper in the crotch region thereof and therewith gather the top sheet together in this region. WO 94/14395 also teaches a corresponding type of transverse barrier in the outer sheet material.

The transverse barriers are intended to prevent faeces discharged to the rear part of the diaper spreading forwards in the diaper and dirtying the wearer's skin and genitals. The barriers also prevent urine and faeces mixing together on the diaper surface, since it is a known fact that the skin is much more sensitive to a mixture of urine and faeces than to each of the two components per se. Faeces contain certain enzymes which are believed to constitute an important factor in irritation of the skin. Urine is also liable to produce ammonia in the presence of faeces, therewith increasing the Ph, which in turn increases the enzymatic activity of said enzymes.

However, such transverse barriers are unable to prevent urine from spreading to the rear parts of the diaper via the underlying absorbent body and there being mixed with faeces, resulting in the aforesaid degradation products which are liable to cause skin irritation problems.

THE OBJECT OF THE INVENTION AND ITS MOST SIGNIFICANT CHARACTERISTIC FEATURES

The object of the present invention is to provide an absorbent article, such as a diaper or an incontinence guard, with which urine and faeces are kept separate most effectively both on the top sheet and in the underlying absorbent body. This object has been achieved by providing in the absorbent body at a position essentially opposite the top sheet barrier a liquid barrier which prevents transportation of liquid in the absorbent body from the front part of the article to its rear part, either completely or partially and at least in those upper parts of the absorbent body that lie proximal to the wearer.

BRIEF DESCRIPTION OF THE DRAWINGS

The invention will now be described in more detail with reference to exemplifying embodiments thereof and also with reference to the accompanying drawings.

FIG. 3 is a schematic longitudinal section view of the diaper shown in FIG. 2.

FIGS. 4 and 5 are respective schematic longitudinal section views of an absorbent body according to two embodiments.

DESCRIPTION OF EMBODIMENTS

Figure 1:
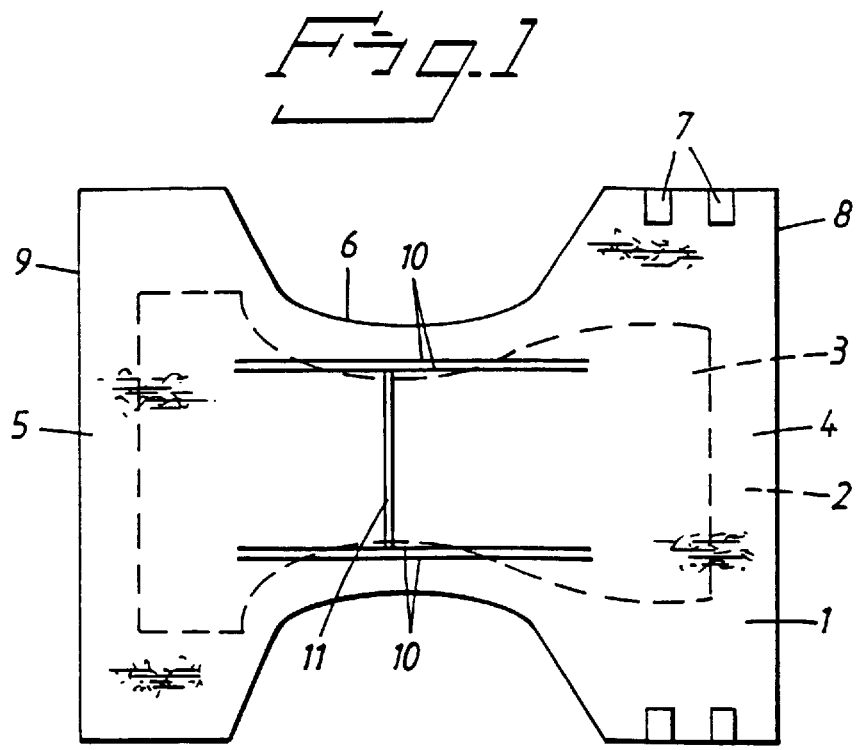
FIG. 1 is a view of a diaper from above, as seen from the side that lies proximal to the wearer.

The diaper illustrated in FIG. 1 indicates a liquid-permeable casing sheet 1, made for instance from nonwoven or perforated plastic film, a liquid-impermeable casing sheet 2, made for instance from plastic film or hydrophobic nonwoven fabric, and an absorbent body 3 which is enclosed between the two casing sheets 1 and 2.

The diaper is intended to be worn around the lower part of the wearer's trunk as a pair of absorbent pants. The diaper has a rear part 4 which, in use, lies rearwardly of the wearer, a front part which, in use, extends forwardly of the wearer, and a narrower crotch part 6 which is located between the rear part 4 and the front part 5 and which is intended to be placed in the wearer's crotch between the wearer's thighs. To enable the diaper to be fastened in the desired pants-like form, fastener tapes 7 are provided in the proximity of the rear waist edge 8 of the diaper. In use, the fastener tapes or tabs 7 are fastened to the outer surface of the front diaper part 5, close to the front waist edge 9, such as to hold the diaper together around the wearer's waist. Naturally, other fastening devices, such as Velcro® fasteners, hooks and eyes, etc. are conceivable.

The diaper illustrated in FIG. 1 also includes pre-tensioned elastic devices 10, which may be comprised of any suitable material, such as elastic foam, elastic ribbons, bands or covered elastic threads. For the sake of simplicity, the elastic devices have been shown in a stretched state in FIG. 1. However, immediately the stretch in the elastic devices is relaxed, the devices will contract and therewith form elastic edges around the leg openings of the diaper.

It will be understood that the illustrated diaper is merely a non-limiting exemplifying embodiment. For example, the shape of the diaper and its construction in general may be varied. For instance, in the case of diapers that are intended to be supported within special tightly-fitting pants, the fastener devices, i.e. the fastener tapes 7, can be omitted, and possibly also the elastic devices 10. The fastening devices are also omitted in so-called pant diapers or training pants.

A transverse barrier 11 is provided in the crotch region of the diaper and extends generally transversely to the longitudinal direction of the diaper. The barrier has an upward extension (height) towards the wearer and is intended to prevent faeces spreading from the rear diaper part 4 to the front diaper part 5, and to prevent urine spreading along the top sheet 1 from said front part to said rear part.

The top sheet barrier 11 may extend transversely across the diaper in a straight or a curved line and may be constructed in a known manner and, for instance, consist in a fold formation in the top sheet or in separate strips of material mounted on the top sheet, such as strips of plastic foam or strips or nonwoven, which may optionally be provided with an elastic device along the outer free edge so as to impart a lifting effect to the strip.

Figure 2:
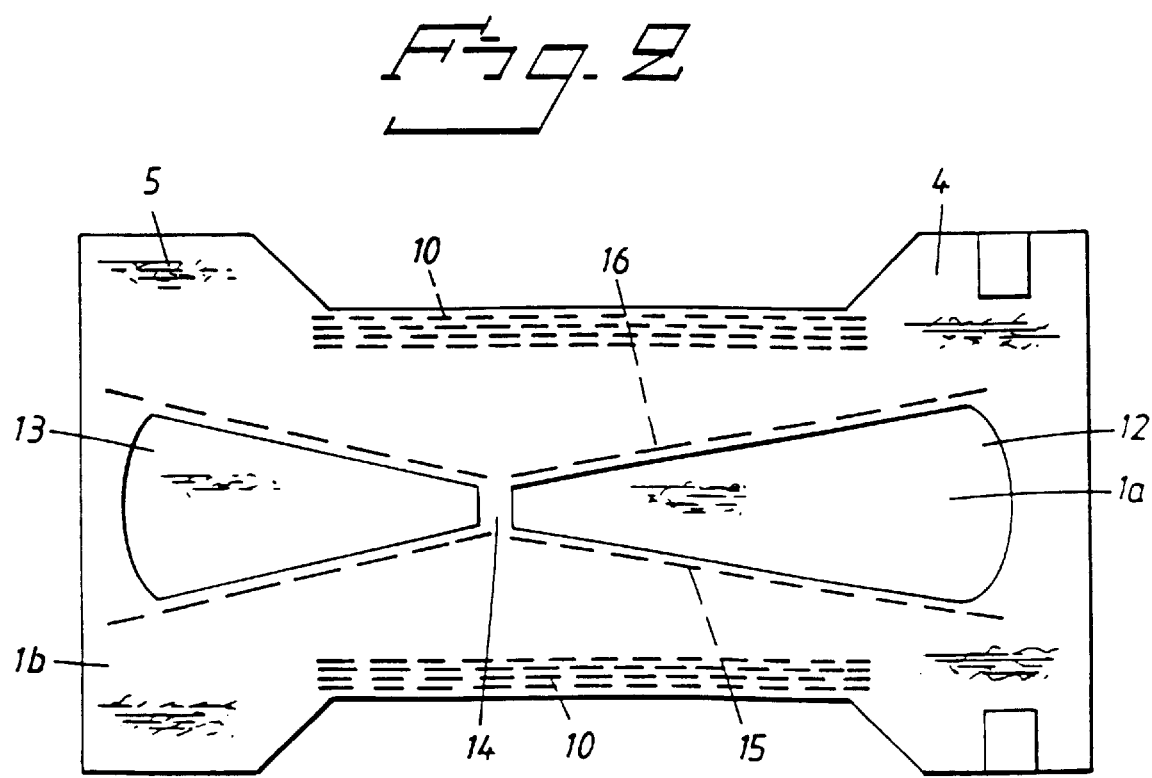
FIG. 2 is a corresponding view from above of another embodiment of a diaper.

The embodiment illustrated in FIGS. 2 and 3 corresponds to the subject of Swedish Patent Application 9400916-4 and has a casing sheet that includes an inner casing sheet 1a and an outer top sheet 1b on that side of the absorbent body 3 which lies proximal to the wearer in use, i.e. the inner casing sheet 1a lies proximal to the absorbent body 3 and the outer top sheet 1b lies proximal to the wearer in use. The outer top sheet 1b may either be comprised of liquid-permeable or liquid-impervious skin-friendly material. This diaper is also provided with leg elastic 10.

The top sheet includes two openings 12 and 13 which are elongated in the longitudinal direction of the diaper. That region 14 of the outer top sheet 1b which lies between the openings 12 and 13 is located between the faeces discharge point and the wetting point, i.e. those regions of the diaper in which faeces and urine are delivered thereto when the diaper is positioned correctly.

Two elastic threads 15, 16 are fastened in a stretched state to the outer top sheet 1b and extend from the front diaper part to the rear diaper part along the side edges of the openings 12 and 13 in the manner described in more detail in Swedish Patent Application 9400916-4.

A tubular body 17 is mounted in a flattened state in the top sheet region 14, between the top sheet 1b and the inner casing sheet 1a, and extends transversely between the points of attachment of the top sheet 1b to the bottom sheet 2 and the inner casing sheet 1a. The top and bottom sides of the tubular body 17 are fastened respectively to the top sheet 1b and the inner casing sheet 1a with the aid of a glue bead, by ultrasonic welding or by like means, for instance.

The tubular body 17 may be comprised of a liquid-permeable or liquid-impermeable material and is preferably made of the same material as the bottom sheet, the inner casing sheet or the top sheet. Instead of using a tubular body 17, the barrier between the openings 12, 13 may alternatively be comprised of a single wall of flexible material which is mounted in a folded state between the inner casing sheet and the top sheet and fastened to said sheets in a manner corresponding to the fastening of the tubular body 17.

The barrier may alternatively be formed by pleats or folds produced in the inner casing sheet or in the top sheet, as also described in Swedish Patent Application 9400916-4.

Generally opposite the barrier 11 and 17 respectively, there is provided in the absorbent body 3 a liquid barrier which prevents liquid spreading from the upper sheet of the absorbent body from its front to its rear part, either completely or to a substantial extent.

The embodiments illustrated in FIGS. 4 and 5 include an absorbent body 3 which comprises three different sheets or layers, an upper acquisition layer 18, an intermediate storage layer 19 and a bottom liquid-dispersion layer 20. The acquisition layer 18 is conveniently comprised of an absorbent material having a relatively large pore size, high wet resilience and low liquid-dispersion ability, such as mechanical cellulose fluff pulp, thermomechanical or chemithermomechanical cellulose fluff pulp (CTMP), chemically stiffened cellulose fibres, synthetic fibres, absorbent foam material, etc.

The major part of the absorbent material in the storage layer 19 is comprised of fluff pulp or some other fibre material of relatively small pore volume and high liquid-dispersion capacity. Chemically produced fluff pulps, which are comprised of fine fibres of essentially pure cellulose, generally have a high liquid-dispersion ability. Fluff pulp, for instance CTMP pulp, compressed to a density greater than about 0.12 g/cm$^3$, also has a relatively good liquid-dispersion ability. Another material which exhibits good liquid-dispersion properties is compressed dry-formed sheet pulp of, e.g., CTMP, or chemical pulp. Such material is described in WO 89/00605. Absorbent foam materials may also be used.

The fibre material in the dispersion layer will preferably comprise mostly of chemical fluff pulp, dry-formed sheet pulp in accordance with the above, or of some other fibre material that has good dispersion properties.

The acquisition layer and the storage layer may include a certain amount of superabsorbent, whereas the dispersion layer is preferably free from superabsorbent or contains only very small quantities of superabsorbent.

In the embodiments illustrated in FIGS. 4 and 5, the front part 18a of the acquisition layer 18 is thinner than the rear part 18b thereof. In the FIG. 4 embodiment, this increase in thickness takes place in a single step, whereas in the FIG. 5 embodiment the thickness of the acquisition layer increases successively from a region that lies immediately behind the anticipated wetting point of the diaper. The thinner front part 18a ha a high density than the thicker rear part 18b. The higher density of the thinner front part 18a is obtained automatically when compressing the absorbent body, due to the reversed thickness relationship of the underlying storage layer 19, provided that this layer has a higher compression resistance than the acquisition layer 18. The compression resistance of a fluff pulp body depends on the type of pulp concerned and the amount of superabsorbent contained therein, among other things.

As a result of the higher density of the front part 18a, said front part will have a smaller mean pore size than the rear part 18b. Since the capillary force increases with decreasing pore sizes, the liquid discharged to the front part of the receiving layer 18a will not spread to the rear part 18b to any great extent, but will be transported immediately into the underlying storage layer 19. The rear part 18b of the acquisition layer will thereby remain mostly dry.

As illustrated in FIGS. 4 and 5, a mechanical liquid barrier 21 may be provided as a complement to the difference in pore size, e.g. in the form of a plastic strip or a strip of some other liquid-impervious or hydrophobic material provided in the acquisition layer 18, between the front and the rear parts 18a and 18b. Such a mechanical liquid barrier 21 will prevent liquid leaking to the rear part 18b of the receiving layer should the front part 18a be temporarily saturated. The liquid barrier 21 may be separate from or integral with the barrier 11 or 17 in the top sheet.

When a mechanical liquid barrier 21 is used in the acquisition layer 18, there is no need for the differences in pore size between the front and the rear parts 18a and 18b in order to prevent the transportation of liquid between said parts. However, an advantage is gained when the rear part 18b includes a material having a relatively large pore size in order to prevent rewetting from the underlying storage layer 19. Furthermore, an advantage is gained when the rear part 18b is able to absorb loose faeces effectively.

As before mentioned, the difference in pore size between the front and the rear parts 18a and 18b of the acquisition layer can be obtained by differences in the density between said parts, although a difference in pore size can also be obtained with one and the same density by using different types of fibre material in the different parts. Polymeric foams of varying pore sizes can also be used in addition to fibre-based absorbent materials.

A liquid barrier can also be provided in the acquisition layer 18, by compressing a stripe in the material.

The liquid barrier will preferably not extend through the full thickness of the absorbent body, but will preferably be restricted to its upper sheet or layer. This will enable liquid to still spread in the bottom layer of the absorbent body, i.e. in the storage and the dispersion layer. It is important that the upper surface of the absorbent body proximal to the wearer is kept dry.

By providing in the top sheet a barrier which prevents faeces from spreading from the rear diaper part to its front part, and by providing in the upper layer of the absorbent body a liquid barrier which prevents liquid from spreading in said layer from the front to the rear part thereof as proposed in accordance with the invention, urine and faeces are separated highly effectively in the diaper, therewith preventing the formation of certain skin-irritating degradation products which are otherwise formed when urine and faeces mix.

Another advantage that can be obtained by keeping the upper layer of the absorbent body dry in the rear part of the diaper is that this will enable different types of top sheet to be used in the front and in the rear part of the diaper respectively. For instance, a conventional casing material can be chosen for the front part, this material isolating the skin from the liquid in the absorbent body, while choosing a hydrophilic absorbent casing material for the rear part, this material being suitable for absorbing loose faeces, for instance fabric or nonwoven comprised of rayon, cotton or other hydrophilic natural fibres.

The invention is, of course, not restricted to the illustrated embodiments thereof since a number of variants are conceivable within the scope of the following claims.

What is claimed is:

1. An absorbent article comprising:

a liquid-permeable top sheet, a liquid-impermeable bottom sheet, and an absorbent body enclosed therebetween, the top sheet includes a transverse barrier which divides the article into a front part and a rear part and which is intended to prevent faeces delivered to the rear part from moving to the front part, the absorbent body includes a liquid barrier which is located essentially opposite the first-mentioned barrier in the top sheet and which prevents, either completely or partially, the transportation of liquid in the absorbent body from the front part of the article to the rear part thereof, at least in the upper parts of the absorbent body that lie proximal to the wearer, wherein the liquid barrier is located inside the absorbent body and the liquid barrier does not extend completely through the absorbent body but only extends in the upper parts of the absorbent body that lie proximal to the wearer.

2. The absorbent article according to claim 1, wherein said liquid barrier is produced by virtue of a difference in mean pore size in the absorbent material, such that at least in the upper layer of the absorbent body proximal to the wearer, liquid is prevented by capillary action from spreading, either totally or partially, from the front part of the layer to its rear part, at least provided that the front part is not saturated with liquid.

3. The absorbent article according to claim 2, wherein the absorbent body includes a first layer adjacent the top sheet and a second layer adjacent the bottom sheet, and the liquid barrier extends completely through the first layer and does not extend into the second layer.

4. The absorbent article according to claim 1, wherein said liquid barrier includes a strip of liquid-impervious maternal, which is either separate from or integral with the top sheet barrier.

5. The absorbent article according to claim 4, wherein the absorbent body includes a first layer adjacent the top sheet and a second layer adjacent the bottom sheet, and the liquid barrier extends completely through the first layer and does not extend into the second layer.

6. The absorbent article according to claim 1, wherein the liquid barrier includes a strip of hydrophobic material which is either separate from or integral with the top sheet barrier.

7. The absorbent article according to claim 6, wherein the absorbent body includes a first layer adjacent the top sheet and a second layer adjacent the bottom sheet, and the liquid barrier extends completely through the first layer and does not extend into the second layer.

8. The absorbent article according to claim 1, wherein said liquid barrier includes a compression stripe in the absorbent material.

9. The absorbent article according to claim 8, wherein the absorbent body includes a first layer adjacent the top sheet and a second layer adjacent the bottom sheet, and the liquid barrier extends completely through the first layer and does not extend into the second layer.

10. The absorbent article according to claim 1, wherein the absorbent body includes an acquisition layer which lies proximal to the wearer, and one or more underlying storage and dispersion layers wherein said liquid barrier extends essentially only through the acquisition layer.

11. The absorbent article according to claim 10, wherein the front part of the acquisition layer has a higher density than the rear part of said layer.

12. The absorbent article according to claim 11, wherein the density of the rear part of the acquisition layer decreases successively in a rearward direction.

13. The absorbent article according to claim 12, wherein the absorbent body includes a first layer adjacent the top sheet and a second layer adjacent the bottom sheet, and the liquid barrier extends completely through the first layer and does not extend into the second layer.

14. The absorbent article according to claim 10, wherein the front and the rear parts of the acquisition layer include different types of absorbent structures having different pore sizes.

15. The absorbent article according to claim 14, wherein the absorbent body includes a first layer adjacent the top sheet and a second layer adjacent the bottom sheet, and the liquid barrier extends completely through the first layer and does not extend into the second layer.

16. The absorbent article according to claim 1, wherein the liquid-permeable top sheet that lies proximal to the wearer in use is comprised of mutually different kinds of material in the front part and the rear part of the article respectively, wherein the rear part of the top sheet is comprised of a hydrophilic material suitable for absorbing loose faeces, e.g. fabric or nonwoven comprised of rayon, cotton or some other hydrophilic natural fibre, whereas the front part of the top sheet is constructed to insulate the wearer's skin from the liquid absorbed in the absorbent body.

17. The absorbent article according to claim 16, wherein the absorbent body includes a first layer adjacent the top sheet and a second layer adjacent the bottom sheet, and the liquid barrier extends completely through the first layer and does not extend into the second layer.

18. The absorbent article according to claim 1, wherein the liquid barrier divides a first part of the absorbent body from a second part of the absorbent body.

19. The absorbent article according to claim 18, wherein the absorbent body includes a first layer adjacent the top sheet and a second layer adjacent the bottom sheet, and the liquid barrier extends completely through the first layer and does not extend into the second layer.

20. The absorbent article according to claim 1, wherein the absorbent body includes a first layer adjacent the top sheet and a second layer adjacent the bottom sheet, and the liquid barrier extends completely through the first layer and does not extend into the second layer.

21. The absorbent article according to claim 1, wherein the absorbent article is a diaper.

22. The absorbent article according to claim 1, wherein the absorbent article is a pant diaper.

23. The absorbent article according to claim 1, wherein the absorbent article is an incontinence guard.

* * * * *